United States Patent
York et al.

(10) Patent No.: US 9,504,991 B2
(45) Date of Patent: Nov. 29, 2016

(54) PROCESS FOR PRODUCTION OF A SILICA-SUPPORTED ALKALI METAL CATALYST

(71) Applicant: Lucite International UK Limited, Southampton (GB)

(72) Inventors: Ian Andrew York, Redcar (GB); Trevor Huw Morris, Redcar (GB)

(73) Assignee: LUCITE INTERNATIONAL UK LIMITED, Southhampton (GB)

( * ) Notice: Subject to any disclaimer, the term of this patent is extended or adjusted under 35 U.S.C. 154(b) by 0 days.

(21) Appl. No.: 14/432,430

(22) PCT Filed: Oct. 1, 2013

(86) PCT No.: PCT/GB2013/052549
§ 371 (c)(1),
(2) Date: Mar. 30, 2015

(87) PCT Pub. No.: WO2014/053818
PCT Pub. Date: Apr. 10, 2014

(65) Prior Publication Data
US 2015/0238942 A1    Aug. 27, 2015

(30) Foreign Application Priority Data

Oct. 1, 2012   (GB) .................................. 1217541.0

(51) Int. Cl.
*B01J 23/92* (2006.01)
*B01J 23/04* (2006.01)
(Continued)

(52) U.S. Cl.
CPC ................. *B01J 23/92* (2013.01); *B01J 23/04* (2013.01); *B01J 38/485* (2013.01); *B01J 38/64* (2013.01); *C07C 51/353* (2013.01); *G06F 11/3632* (2013.01); *G06F 11/3656* (2013.01); *Y02P 20/584* (2015.11)

(58) Field of Classification Search
CPC .................................. B01J 23/90; B01J 23/92
See application file for complete search history.

(56) References Cited

U.S. PATENT DOCUMENTS 3,743,607 A * 7/1973 Sennewald .............. B01J 23/52
502/170
4,478,948 A   10/1984 Rebsdat et al.
(Continued)

FOREIGN PATENT DOCUMENTS

GB      1473217         5/1977
WO      99/52628        10/1999
WO      2009/003722 A1  1/2009

OTHER PUBLICATIONS

Mamoru Al, "Formation of methyl methacrylate by condensation of methyl propionate with formaldehyde over silica-supported cesium hydroxide catalysts", Applied Catalysis, vol. 288, No. 1-2, p. 211-215, (2005) (5 pages).
(Continued)

*Primary Examiner* — Anthony J Zimmer
(74) *Attorney, Agent, or Firm* — Shumaker, Loop & Kendrick, LLP

(57) ABSTRACT

A process for regenerating a silica-supported depleted alkali metal catalyst is described. The level of alkali metal on the depleted catalyst is at least 0.5 mol % and the silica support is a zero-gel. The process comprises the steps of contacting the silica supported depleted alkali metal catalyst with a solution of a salt of the alkali metal in a solvent system that has a polar organic solvent as the majority component. A re-impregnated catalyst prepared by the process of the invention any comprising a silica zero-gel support and a catalytic metal selected from an alkali metal in the range 0.5-5 mol % on the catalyst, wherein the surface area of the silica support is <180 m²/g is also described. The invention is applicable to a process for preparing an ethylenically unsaturated acid or ester comprising contacting an alkanoic acid or ester of the formula $R^1$—$CH_2$—$COOR^3$, with formaldehyde or a suitable source of formaldehyde.

19 Claims, 1 Drawing Sheet

(51) Int. Cl.
  *B01J 38/64* (2006.01)
  *C07C 51/353* (2006.01)
  *B01J 38/48* (2006.01)
  *G06F 11/36* (2006.01)

(56) References Cited

U.S. PATENT DOCUMENTS

| | | | | |
|---|---|---|---|---|
| 4,526,714 | A | * | 7/1985 | Feijen ................ A61L 33/0011 424/423 |
| 4,942,258 | A | | 7/1990 | Smith |
| 4,990,662 | A | | 2/1991 | Hagen et al. |
| 6,887,822 | B2 | | 5/2005 | Hu |
| 2003/0166949 | A1 | * | 9/2003 | Manzer ................ C07D 307/58 549/327 |
| 2007/0167639 | A1 | * | 7/2007 | Evans ...................... B01J 23/50 549/538 |

OTHER PUBLICATIONS

International Search Report for PCT/GB2013/052549 mailed Jan. 3, 2014, (4 pages).

* cited by examiner

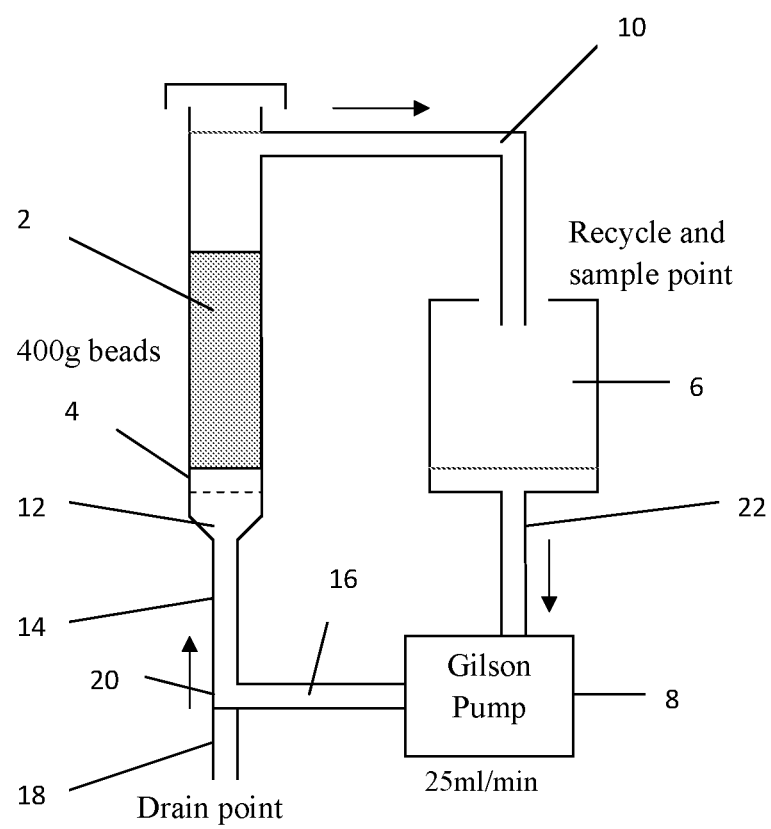

PROCESS FOR PRODUCTION OF A SILICA-SUPPORTED ALKALI METAL CATALYST

CROSS-REFERENCE TO RELATED APPLICATION

This 35 U.S.C. §371 U.S. National Stage filing claims priority to PCT/GB2013/052549 filed Oct. 1, 2013, which claims priority to GB Application No. 1217541.0 filed on Oct. 1, 2012, the contents each of which are incorporated by reference herein.

TECHNICAL FIELD AND BACKGROUND

The present invention relates to the production of alkali metal catalysts on silica supports, particularly the regeneration of alkali metal depleted catalysts.

Alkali metal catalysts on silica supports are known to be useful in catalysing various chemical processes. For instance, the alkali metal caesium catalyses the aldol condensation of formaldehyde with alkyl esters or acids to produce ethylenically unsaturated esters or acids, in particular with methyl propionate to form methyl methacrylate (MMA) and methacrylic acid (MA). However, in continuous industrial applications, the catalytic metal component and catalytic surface area are slowly depleted over time causing consequential loss of catalyst activity. It would be advantageous, therefore, to be able to regenerate the catalyst.

WO99/52628 discloses caesium doped silica supported catalysts. WO99/52628 teaches that for the catalyst to be most effective the surface area should be maintained. The document goes on to teach the general process of impregnation mentioning various salts. No specific solvent is given for caesium except water.

U.S. Pat. No. 4,990,662 discloses the use of metal salts during the process of impregnation. The impregnation of a support with Rb, Cs, K and Na phosphates in aqueous solution by "incipient wetness" or the "pore filling technique" is described. Caesium carbonate is also used and added during catalyst preparation by an unspecified method. This patent also describes a method of adding caesium to the catalyst as part of the vaporized feed to avoid depletion of the catalyst. This technique has the disadvantage of poor distribution of the caesium on the catalyst and excessive coke formation at the front face of the catalyst bed.

U.S. Pat. No. 6,887,822 (PQ Corporation) describes production of a silica hydrogel supported alkali or alkaline earth metal catalyst by impregnation of the hydrogel with an aqueous alkaline solution of the alkali or alkaline earth metal salt. However, the document also teaches that the silica gel surface area is reduced at alkaline pH and elevated temperatures.

WO2009/003722 teaches the impregnation of the catalytic metal onto inorganic oxide supports such as silica using an aqueous acid bath.

BRIEF SUMMARY

Surprisingly, a process has been found which restores catalyst activity to original levels without surface area treatment or damage to the catalyst support.

According to the present invention there is provided a process for regenerating a silica-supported depleted alkali metal catalyst wherein the level of alkali metal on the depleted catalyst is at least 0.5 mol %, and wherein the silica support is a zero-gel comprising the step of:—contacting said silica supported depleted alkali metal catalyst with a solution of a salt of the alkali metal in a solvent system that has a polar organic solvent as the majority component.

DETAILED DESCRIPTION

The process of the invention is particularly suitable for regeneration of a used silica-supported catalyst. Such catalysts will typically have a reduced surface area. For instance, the depleted and subsequently regenerated catalyst may have a surface area of $<180\ m^2/g^{-1}$, more typically $<150\ m^2\ g^{-1}$. The surface area may be measured by well known methods, a preferred method being a standard BET nitrogen absorption method as is well known in the art. Preferably, the bulk of the surface area of the silica is present in pores of diameter in the range 5-150 nm. Preferably, the bulk of the pore volume of the silica is provided by pores of diameter in the range 5-150 nm. By the "bulk" of its pore volume or surface area is provided by pores of diameter in the range 5-150 nm we mean that at least 50% of the pore volume or surface area is provided by pores of this diameter and more preferably at least 70%.

In addition, the depleted alkali metal catalyst may additionally include a second or further metal selected from the group consisting of zirconium, titanium, hafnium, aluminium, boron, and magnesium or mixtures thereof, preferably, zirconium, titanium, hafnium and aluminium or mixtures thereof, most preferably, hafnium and zirconium or mixtures thereof.

Suitable alkali metals may be selected form lithium, sodium, potassium, rubidium and caesium, preferably, potassium, rubidium and caesium. Caesium is preferred. The salt of the alkali metal may be selected from the group consisting of acetate, propionate, carbonate, hydrogen carbonate, nitrate and hydroxide.

Surprisingly, it has been found that strongly alkaline salts, for example alkali metal hydroxides such as caesium hydroxide may be used to re-impregnate the catalyst. This is surprising because it was understood from U.S. Pat. No. 6,887,822 that exposing the catalyst support to strongly alkaline salts would lead to hydrothermal ageing of the support with consequential damage to the catalyst and loss of surface area. In addition, exposing the catalyst to alkaline salts could lead to dissolution of the silica.

It has been found to be advantageous to use an impregnation solvent system that has a polar organic solvent as the majority component to act as carrier for the alkali metal salt in the impregnation. This solvent system advantageously reduces heat generation, which can cause catalyst bead cracking, and also reduces the risk of silica dissolution at high pH. Surprisingly, this is also contrary to the prior art teaching. U.S. Pat. No. 6,887,822 teaches that using an alcoholic solution of caesium for re-impregnation on a zero gel causes a high amount (76%) of bead cracking. In the current invention, it is found that doing the same on a depleted catalyst causes no such problems.

A preferred polar organic solvent is an alcohol such as a $C_1$-$C_4$ alkanol, especially, methanol. This polar organic solvent can be used alone as the solvent system or mixed with an aliphatic ester, and/or with water. The aliphatic ester may be a $C_1$-$C_6$ alkyl $C_1$-$C_6$ alkanoate, more typically a $C_1$-$C_4$ alkyl $C_1$-$C_4$ alkanoate, most typically, methyl propionate. Particularly suitable systems are provided wherein the polar organic solvent is methanol and the aliphatic ester is methyl propionate such as the azeotropic mixture thereof or wherein the polar organic solvent is methanol. In either case, the solvent system may take up progressively more water as the impregnation progresses mainly due to water being already present on the catalyst to be treated but also due to the introduction of water in an aqueous source solution of the alkali metal salt prior to its addition to the polar organic solvent and also due to a small amount that is liberated from the reaction with the support. In a series of batch reactions, it will be appreciated that the solvent system will gradually be enriched in water as new catalyst batches are impregnated and as alkali metal salt is added to replenish the solvent system. The preferred solvent system commences with methanol without the use of significant levels of aliphatic ester. Typically, methanol is used in conjunction with a caesium salt, more typically caesium hydroxide. The use of such a combination causes water to be progressively added and taken up into the solvent system during impregnation as explained above.

Preferably, the solution of the alkali metal salt in the solvent system has a starting pH between 8 and 13, more preferably, the solution of the alkali metal salt in the solvent system has a starting pH between 12 and 13.

As mentioned above, a preferred salt is the hydroxide and the preferred polar organic solvent is methanol.

A suitable concentration for the alkali metal in the solvent system at the start of the impregnation is between $6 \times 10^{-3}$ and 0.6 mol·dm$^{-3}$ alkali metal in the solution, more typically, between $18 \times 10^{-3}$ and 0.18 mol·dm$^{-3}$ alkali metal in the solution, most typically, $30 \times 10^{-3}$ and 0.12 mol·dm$^{-3}$ alkali metal in the solution.

Typically, the contacting step duration is sufficient to equilibrate the catalyst support with the solution. Equilibration may be determined by no significant change in the alkali metal levels in the solution resulting from further contact with the support. By significant change is meant changes in the concentration of −5% or more, more typically, −1% or more. Typically, equilibration may be undertaken in a few hours.

According to a second aspect of the present invention there is provided a re-impregnated catalyst prepared by the process of the first aspect of the invention optionally including any of the preferred or optional features thereof comprising a silica zero-gel support and a catalytic metal selected from an alkali metal in the range 0.5-5 mol % on the catalyst, wherein the surface area of the silica support is <180 m$^2$/g.

In one embodiment, the catalyst contains between 0.5 and 2.0 wt % of the second metal. A particularly preferred second metal is zirconium. The second metal improves the catalyst crush resistance as described in U.S. Pat. No. 6,887,822.

In the case where it is desired to impregnate a silica-supported catalyst with caesium using methanol as the solvent, any methanol soluble caesium salt can be used, such as the carbonate, hydrogen carbonate, acetate, nitrate or propionate. The adsorption of caesium is found to proceed most efficiently at high pH~13 and to reduce with falling pH necessitating the use of a greater concentration of caesium salt in solution. Accordingly, the adsorption of caesium proceeds most efficiently when a strongly basic caesium salt such as caesium hydroxide is used.

Surprisingly, the presence of water in the impregnation solution has no effect on the caesium uptake efficiency. In this regard, the presence of water has been tested up to 44 wt % and found to have no appreciable effect.

Water may typically be present in the impregnation solution at up to 40% by weight, more typically, up to 30% by weight in solution, most typically, up to 20% by weight.

In addition, significant levels of silica dissolution are avoided when low levels of alkali metal salt <2 wt % in solution are used.

Surprisingly, a used catalyst that has a depleted surface area of <180 m$^2$/g, more usually, <150 m$^2$/g, and that has been regenerated by adding more alkali metal as defined herein performs similarly in terms of % MMA & MAA yield and % MMA & MAA selectivity to a freshly prepared catalyst of high surface area (>250 m$^2$/g) containing the same amount of alkali metal. This represents a considerable improvement in performance over that achieved before catalyst regeneration.

Typically, the level of alkali metal on the depleted catalyst prior to impregnation is at least 0.5 mol %, more typically, at least 1.0 mol %. Upper levels for the alkali metal on the depleted catalyst prior to impregnation will depend on the reaction for which the catalyst has been used. The level will be a depleted level for that reaction. Typically, the alkali metal will be present at a level of 0.5-3.0 mol %, more typically, 1-3.0 mol % on the depleted catalyst.

Alternatively, the wt % of alkali metal may be at least 1 wt % or more typically, at least 2 wt % on the depleted catalyst. Typically, the alkali metal is present in the range 1 to 6 wt % on the depleted catalyst, more typically, 2-6 wt %, especially 4-6 wt %. These amounts would apply to all alkali metals but especially caesium.

Typically, the level of alkali metal in the catalyst after carrying out the process of the invention is in the range from 1-5 mol % on the catalyst, more typically, 2-4 mol %, most typically, 2.5-4 mol % on the catalyst.

Alternatively, the re-impregnated catalyst may have a wt % of alkali metal in the range 1 to 10 wt % on the catalyst, more typically 4 to 8 wt %, most typically, 5-8 wt %. These amounts would apply to all alkali metals but especially caesium.

The increase in alkali metal on the catalyst following the process of the invention is typically in the range 0.25 to 2.0 mol % on the catalyst, more typically, 0.75 mol % to 1.5 mol %, most typically, 0.9 to 1.4 mol %.

Alternatively, the typical increase in alkali metal is between 0.5 and 4 wt % on the catalyst, more typically, between 1.5 and 3.5 wt %, most typically, between 2 and 3 wt %. These amounts would apply to all alkali metals but especially caesium.

According to a third aspect of the present invention there is provided a process for preparing an ethylenically unsaturated acid or ester comprising contacting an alkanoic acid or ester of the formula R$^1$—CH$_2$—COOR$^3$, with formaldehyde or a suitable source of formaldehyde of formula I as defined below:

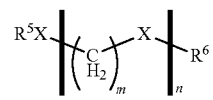

I where R$^5$ is methyl and R$^6$ is H;
X is O;
n is 1;
and m is 1;
in the presence of a catalyst according to the second aspect of the present invention, and optionally in the presence of an alkanol; wherein R$^1$ is hydrogen or an alkyl group with 1 to 12, more preferably, 1 to 8, most preferably, 1 to 4 carbon atoms and R$^3$ may also be independently, hydrogen or an alkyl group with 1 to 12, more preferably, 1 to 8, most preferably, 1 to 4 carbon atoms.

Preferably, the ethylenically unsaturated acid or ester is selected from methacrylic acid, acrylic acid, methyl methacrylate, ethyl acrylate or butyl acrylate, more preferably, it is an ethylenically unsaturated ester, most preferably, methyl methacrylate. Accordingly, the preferred ester or acid of formula $R^1$—$CH_2$—$COOR^3$ is methyl propionate or propionic acid respectively and the preferred alkanol is therefore methanol. However, it will be appreciated that in the production of other ethylenically unsaturated acids or esters, the preferred alkanols or acids will be different.

Accordingly, one particular process for which the re-impregnated catalysts of the present invention have been found to be particularly advantageous and/or from which the depleted catalysts may be obtained is the condensation of formaldehyde with methyl propionate in the presence of methanol to produce MMA.

In the case of production of MMA, the re-impregnated catalyst is preferably contacted with a mixture comprising formaldehyde, methanol and methyl propionate.

Preferably, the mixture comprising formaldehyde, methanol and methyl propionate contains less than 5% water by weight. More preferably, the mixture comprising formaldehyde, methanol and methyl propionate contains less than 1% water by weight. Most preferably, the mixture comprising formaldehyde, methanol and methyl propionate contains 0.1 to 0.5% water by weight.

The term "alkyl" when used herein, means unless otherwise indicated, $C_1$ to $C_{10}$, preferably, $C_1$ to $C_4$ alkyl, and alkyl includes methyl, ethyl, propyl, butyl, pentyl, hexyl, and heptyl groups and is most preferably methyl.

In the third aspect of the present invention, the alkanoic acid or ester thereof and formaldehyde can be fed, independently or after prior mixing, to the reactor containing the catalyst at molar ratios of acid or ester to formaldehyde of from 20:1 to 1:20 and at a temperature of 250-400° C. with a residence time of 1-100 seconds and at a pressure of 1-10 bara.

In the first aspect of the present invention, the re-impregnation may be carried out under any suitable conditions, for example, ambient temperatures and pressures. Suitable temperatures are 0-100° C., more typically 5-60° C., most typically, 10-50° C. Suitable pressures for the reaction are 1-10 bara.

Typically, the catalyst is in the form of a fixed bed during contact with the alkali metal solution which are thereby passed therethrough.

Suitable flow rates for the alkali metal solution in contact with the catalyst are 0.1 to 10 bed volumes/hr, more typically 0.2 to 2 bed volumes/hr, most typically 0.4 to 1 bed volumes/hr.

By bed volume is meant the amount equivalent to the bulk volume of the bed of catalyst to be treated.

By majority component of a solvent system is meant a component that makes up at least 50% by volume of the solvent system, more suitably, at least, 60%, most suitably, 70% or more. The majority component may make up 95% or more, for example, 99% or more, or approximately 100% of the solvent system by volume. If the majority component does not make up 100% by volume of the solvent system, the balance of the solvent system may be made up of one or more co-solvents.

By solvent system herein is meant a single solvent or a solvent together with one or more co-solvents. By single solvent is meant more than 98% by volume, more typically, more than 99% by volume of the solvent system. Accordingly, by co-solvent is meant a solvent that makes up at least 1% by volume of the solvent system, more typically, at least 2% by volume.

By zero-gel is meant a dried support typically, wherein >90% of the water has been removed from the hydrogel, more typically, >95%, most typically, >99%. A zerogel may contain up to 6% water by weight, more usually, 3-5% by weight.

By mol % on the catalyst herein is meant mol % relative to moles of silica ($SiO_2$) in the catalyst. It is therefore assumed for the purpose of calculation that silica has a molecular weight equivalent to $SiO_2$ rather than that of a silica network. This more accurately reflects the nature of the catalyst. For example, 1 wt % caesium would equate to 0.45 mol % caesium in the catalyst, assuming molecular weights of 132.9 and 60.1 respectively.

Unless indicated to the contrary, amounts of alkali metal or alkali metal catalyst relate to the alkali metal ion and not the salt.

Levels of alkali metal on the catalyst whether mol % or wt % may be determined by appropriate sampling and taking an average of such samples. Typically, 5-10 samples of a particular catalyst batch would be taken and alkali metal levels determined and averaged, for example by XRF analysis.

The catalysts will normally be used and re-impregnated in the form of a fixed bed and so it is desirable that the catalyst is formed into shaped units, e.g. spheres, granules, pellets, aggregates, or extrudates, typically having maximum and minimum dimensions in the range 1 to 10 mm. The catalysts are also effective in other forms, e.g. powders or small beads.

It will be appreciated that the process of the invention is a liquid phase impregnation process.

BRIEF DESCRIPTION OF THE DRAWINGS

The invention will now be described by way of example only with reference to the following examples and drawings in which:—

FIG. 1 is a schematic view of apparatus for carrying out the process of the invention.

Referring to FIG. 1, a 2" glass chromatography column 2 has a tapered lower end 12 connecting the column 2 to an inlet tube 14. The inlet tube 14 is connected to Gilson pump 8 via a T connection 20 and pump outlet tube 16. The T connection 20 includes a drain tube 18 which may be used to drain fluid from the column and a switch (not shown) for directing fluid flow from the pump 8 or to the drain tube 18 as required. A pump inlet tube 22 connects the Gilson pump to the base outlet of the reservoir flask 6. A recycling conduit 10 connects the top of the column 2 to the top inlet of the reservoir flask 6 to allow fluid pumped up through the bed to be recycled to the reservoir 6. In the embodiment shown, the column 2 contains 400 g of catalyst beads supported on a frit 4 located across the base of the column. The use of the apparatus will be described more particularly hereafter and with reference to the examples.

Working Examples

Caesium Regeneration of an Exhausted Catalyst

Used Catalyst

In all examples, samples from the same batch of used and depleted caesium on silica/zirconia catalyst beads (5.05 wt % Cs, 0.86 wt % Zr, 130 m²/g) were used. This catalyst, when fresh, had 6.7 wt % Cs on it with 0.86 wt % Zr and had a surface area of 327 m$^2$/g. pH measurements, where quoted, were made by adding an equal volume of water to a sample of solution and observing the colour change in a pH paper immersed in it.

Example 1

A 1.2 wt % solution of caesium in methanol was prepared using caesium carbonate ($Cs_2CO_3$, 99% Reagent Plus from Aldrich) and dry methanol (<1000 ppm water). 400 g of used catalyst beads were placed in a 2" glass chromatography column 2 with a glass frit 4 at the bottom. 1000 ml of caesium solution in methanol was charged to a 2 liter flask 6 (catalyst: solution ratio $\phi$=0.4 kg/liter) and pumped up-flow at 25 ml/min through the catalyst bed from the bottom of the column by a Gilson pump 8. Solution that had passed through the bed was returned to the flask via a recycling conduit 10 in the column 2 above the level of the catalyst. XRF analysis (Oxford Instruments X-Supreme8000) was used to measure the caesium content in solution for the starting feed and periodic samples of the return flow from the column. The solution was recirculated in this way until XRF analysis showed that a steady-state caesium concentration in solution had been reached, which occurred after 2 hrs, when it was measured at 0.55 wt % (54.1% uptake from solution)

The methanol solution was then drained from the bed under gravity for 1 hour and the catalyst beads dried in situ by passing a current of dry nitrogen up-flow through the bed at ~200 ml/min overnight. 650 ml of the original solution was recovered after draining and the dried catalyst was found to have 6.72 wt % Cs as measured by XRF. Of the 1.67 wt % increase in caesium, 1.28 wt % was calculated to have come from uptake from the solution and 0.39 wt % from evaporation of methanol solution remaining in the pores.

Example 2

The remaining caesium in methanol solution from Example 1 (0.55 wt % Cs, 650 ml) was made up to 1000 ml with fresh methanol and extra caesium carbonate added to increase the concentration of caesium in solution to 1.38 wt %. A fresh 400 g of used catalyst was then regenerated using the same method as Example 1 to yield, after drying, a catalyst with 6.78 wt % caesium on it. The remaining solution contained 0.79 wt % caesium by XRF (42.4% uptake from solution).

Example 3

The remaining caesium in methanol solution from Example 2 (0.79 wt % Cs, 650 ml) was made up to 1000 ml with fresh methanol and extra caesium carbonate added to increase the concentration of caesium in solution to 1.40 wt %. A fresh 400 g batch of used catalyst was then regenerated using the same method as Example 1 to yield, after drying, a catalyst with 6.68 wt % caesium on it. The remaining solution contained 0.93 wt % caesium by XRF (33.5% uptake from solution).

Example 4

The remaining caesium in methanol solution from Example 4 (0.93 wt % Cs, 650 ml) was made up to 1000 ml with fresh methanol and extra caesium carbonate added to increase the concentration of caesium in solution to 1.402 wt %. A fresh 400 g batch of used catalyst was then regenerated using the same method as Example 1 to yield, after drying, a catalyst with 6.73 wt % caesium on it. The remaining solution contained 0.87 wt % caesium by XRF (36.8% uptake from solution).

Example 5

The remaining caesium in methanol solution from Example 4 (0.87 wt % Cs, 650 ml) was made up to 1000 ml with fresh methanol and extra caesium carbonate added to increase the concentration of caesium in solution to 1.361 wt %. A fresh 400 g batch of used catalyst was then regenerated using the same method as Example 1 to yield, after drying, a catalyst with 6.62 wt % caesium on it. The remaining solution contained 0.91 wt % caesium by XRF (33.2% uptake from solution).

Example 6

The remaining caesium in methanol solution from Example 5 (0.91 wt % Cs, 650 ml) was made up to 1000 ml with fresh methanol and extra caesium carbonate added to increase the concentration of caesium in solution to 1.191 wt %. A fresh 400 g batch of used catalyst was then regenerated using the same method as Example 1 to yield, after drying, a catalyst with 6.44 wt % caesium on it. The remaining solution contained 0.79 wt % caesium by XRF (33.6% uptake from solution).

Accordingly, re-cycling of drained equilibrium wash by replenishment with $Cs_2CO_3$/methanol results in a reducing uptake from solution, which results in greater initial concentrations of caesium being required to obtain the same uptake by the catalyst. (Examples 2-6).

Example 7

A sample of used and caesium depleted catalyst from the same batch (5.05 wt % Cs, 0.86 wt % Zr, 130 m$^2$/g) was regenerated using the method of Example 1, but using 300 g of catalyst and 1500 ml of methanol solution (catalyst: solution ratio $\phi$=0.2 kg/liter) containing 0.5 wt % caesium initially at 100 ml/min. After recirculation for 2 hrs 1200 ml of the original solution was recovered, which contained 0.24 wt % caesium by XRF (51.9% uptake from solution). The regenerated catalyst had, after drying, 6.25 wt % caesium on it as measured by XRF. Of the 1.2 wt % increase in caesium, 1.04 wt % was calculated to have come from uptake from the solution and 0.16 wt % from evaporation of methanol solution remaining in the pores.

Accordingly, halving of the catalyst-to-solution ratio, $\phi$, did not significantly affect the proportion of caesium adsorbed during the wash (~50% uptake was observed, in both Examples 1 and 7 with different initial caesium concentrations). (Example 7).

The decrease in excess caesium obtained on the beads after draining and drying is consistent with a decrease in the strength of the equilibrium solution. (Examples 1 to 7).

TABLE 1

Results of Repeated Catalyst Regenerations
using Caesium Carbonate

| Example | Wt % Cs Increase on Catalyst from solution | Wt % Cs Increase on Catalyst from Evaporation of Solution in Pores | Final Wt % Cs Measured on Catalyst by XRF | % Caesium taken up from Solution |
|---|---|---|---|---|
| 1 | 1.28 | 0.39 | 6.72 | 54.1% |
| 2 | 1.16 | 0.57 | 6.78 | 42.4% |
| 3 | 0.93 | 0.70 | 6.68 | 33.5% |
| 4 | 1.02 | 0.66 | 6.73 | 36.8% |
| 5 | 0.89 | 0.68 | 6.62 | 33.2% |
| 6 | 0.79 | 0.60 | 6.44 | 33.6% |
| 7 | 1.04 | 0.16 | 6.25 | 51.9% |

Example 8

1000 ml of a 0.785 wt % solution of caesium in methanol was prepared using 7.84 g $CsOH \cdot H_2O$ as the Cs source with methanol. Karl Fisher measurement of the initial water concentration showed there was 0.284 wt % water present and an approximate pH value of 13.0.

A sample of used catalyst was regenerated using the method of Example 1. After recirculation for 2 hrs the solution contained 0.078 wt % caesium by XRF (90% uptake from solution) and 1.145 wt % water and had a pH of 8.5. The regenerated catalyst had, after drying, 6.71 wt % caesium on it as measured by XRF. Of the 1.66 wt % increase in caesium, 1.4 wt % was calculated to have been taken up from solution and 0.26 wt % from evaporation of methanol solution remaining in the pores.

Accordingly, the use of a high pH wash solution of caesium gives a greater uptake efficiency even from a lower concentration of caesium. (Example 8).

Example 9

1000 ml of a 0.787 wt % solution of caesium in methanol/water (90:10) was prepared using 7.97 g $CsOH \cdot H_2O$ as the Cs source in a 10 wt % water in methanol solvent mixture. Karl Fisher measurement of the initial water concentration showed there was 10.63 wt % water and a pH measurement of 13.0.

A sample of used catalyst was regenerated using the method of Example 1. After recirculation for 2 hrs the solution contained 0.104 wt % caesium by XRF (86.8% uptake from solution) and 10.77 wt % water and had a pH of 8.5. The regenerated catalyst had, after drying, 6.8 wt % caesium on it as measured by XRF. Of the 1.75 wt % increase in caesium, 1.35 wt % was calculated to have been taken up from solution and 0.4 wt % from evaporation of methanol solution remaining in the pores.

Example 10

1000 ml of a 1.56 wt % solution of caesium in water/methanol (water was added to assist dissolution) was prepared using caesium bicarbonate $CsHCO_3$ as the Cs source. Karl Fisher measurement of the initial water concentration showed there was 11.58 wt % water and a pH measurement of 9.0.

A sample of used catalyst was regenerated using the method of Example 1. After recirculation for 2 hrs the solution contained 1.104 wt % caesium by XRF (29.2% uptake from solution) and 13.12 wt % water and had a pH of 7.5. The regenerated catalyst had, after drying, 7.07 wt % caesium on it as measured by XRF. Of the 2.02 wt % increase in caesium, 0.91 wt % was calculated to have been taken up from solution and 1.11 wt % from evaporation of methanol solution remaining in the pores.

Example 11

1000 ml of a 1.18 wt % solution of caesium in methanol was prepared using caesium carbonate ($Cs_2CO_3$, 99% Reagent Plus from Aldrich) and methanol. Karl Fisher measurement of the initial water concentration showed there was 0.167 wt % water and a pH measurement of 12.5.

A sample of used catalyst was regenerated using the method of Example 1. After recirculation for 2 hrs the solution contained 0.54 wt % caesium by XRF (54.2% uptake from solution) and 1.177 wt % water and had a pH of 9.0. The regenerated catalyst had, after drying, 7.05 wt % caesium on it as measured by XRF. Of the 2.0 wt % increase in caesium, 1.27 wt % was calculated to have been taken up from solution and 0.73 wt % from evaporation of methanol solution remaining in the pores.

TABLE 2

Analyses of End Solution after Catalyst Regeneration

| Example | Final wt % Cs in solution by XRF-I | Final wt % $H_2O$ in solution by KF | Initial pH of Solution | Final pH of Solution | Si (ppm) in End Solution by ICP-OES |
|---|---|---|---|---|---|
| 8 - CsOH | 0.078 | 1.145 | 13.0 | 8.5 | 1.0 |
| 9 - CsOH | 0.104 | 10.77 | 13.0 | 8.5 | — |
| 10 - $CsHCO_3$ | 1.104 | 13.12 | 9.0 | 7.5 | 2.6 |
| 11 - $Cs_2CO_3$ | 0.540 | 1.177 | 12.5 | 9.0 | 30 |

Hence, the presence of larger amounts of water in the starting wash solution does not significantly affect the efficiency of caesium uptake. (Example 9).

Partially neutralised caesium salts of lower starting pH exhibit a much lower caesium uptake efficiency than those with higher pH. (Examples 9, 10 and 11).

High pH solutions of caesium salts in the presence of water do not cause significant amounts of silica dissolution at the concentrations used (<0.1 wt % Si).

Catalyst Testing

Regenerated catalysts from Examples 7 to 11 were tested in a lab scale reactor alongside a standard fresh catalyst and the original un-regenerated catalyst. 3 g of each catalyst was heated to 350° C. in a tube reactor and pre-conditioned overnight with a vaporized feed stream comprising 59.4 wt % methyl propionate, 29.7 wt % methanol, 3.9 wt % formaldehyde and 6.9 wt % water supplied from a pre-vaporizer fed by a Gilson pump at 0.032 ml/min. The reactor exit vapor flow was condensed and sampled at five different feed pump rates to obtain conversions at different vapor contact times with the catalyst. The condensed liquid products and the liquid feed were analysed by a Shimadzu 2010 Gas Chromatograph with a DB1701 column. The composition of the samples were then determined from the gas chromatography data and the % yield and % selectivity to methacrylate (MMA+MAA) calculated. The results are shown in Table 3.

The testing of catalysts produced in Examples 7 to 11 show that similar results to fresh catalyst are obtained in terms of % MMA & MAA yield and % MMA & MAA selectivity in the catalysis of formaldehyde condensation with methyl propionate to produce MMA. They also show a considerable improvement when compared with the performance of the caesium depleted, used catalyst before regeneration.

TABLE 3

Results of Regenerated Catalyst Testing

| Example | % MMA + MAA Yield | % MMA + MAA Selectivity | Wt % Cs | SA (m²/g) |
|---|---|---|---|---|
| Fresh | 10 | 96.68 | 6.3 | 327 |
| Before Regeneration | 8* | 95.50 | 5.05 | 130 |
| 7 | 10 | 96.80 | 6.25 | — |
| 8 | 10 | 96.24 | 6.71 | 120.8 |
| 9 | 10 | 96.02 | 6.8 | 112.4 |
| 10 | 10 | 95.95 | 7.07 | 114.9 |
| 11 | 10 | 96.36 | 7.05 | 112.4 |

*Maximum yield obtained at any contact time

Attention is directed to all papers and documents which are filed concurrently with or previous to this specification in connection with this application and which are open to public inspection with this specification, and the contents of all such papers and documents are incorporated herein by reference.

All of the features disclosed in this specification (including any accompanying claims, abstract and drawings), and/or all of the steps of any method or process so disclosed, may be combined in any combination, except combinations where at least some of such features and/or steps are mutually exclusive.

Each feature disclosed in this specification (including any accompanying claims, abstract and drawings) may be replaced by alternative features serving the same, equivalent or similar purpose, unless expressly stated otherwise. Thus, unless expressly stated otherwise, each feature disclosed is one example only of a generic series of equivalent or similar features.

The invention is not restricted to the details of the foregoing embodiment(s). The invention extends to any novel one, or any novel combination, of the features disclosed in this specification (including any accompanying claims, abstract and drawings), or to any novel one, or any novel combination, of the steps of any method or process so disclosed.

The invention claimed is:

1. A process for regenerating a silica-supported depleted alkali metal catalyst wherein a level of alkali metal on the depleted catalyst is at least 0.5 mol %, and wherein the silica support is a zero-gel comprising the step of:
contacting said silica supported depleted alkali metal catalyst with a solution of a salt of the alkali metal in a solvent system that has a polar organic solvent as the majority component.

2. The process according to claim 1, wherein a surface area of the catalyst is <180 m²/g.

3. The process according to claim 1, wherein a bulk of a surface area of the silica is present in pores having a diameter ranging from 5 nm to 150 nm.

4. The process according to claim 3, wherein a bulk of pore volume of the silica is provided by pores having diameters ranging from 5 nm to 150 nm.

5. The process according to claim 1, wherein the alkali metal is selected from lithium, sodium, potassium, rubidium, and caesium.

6. The process according to claim 1, wherein the salt of the alkali metal is selected from the group consisting of acetate, propionate, carbonate, hydrogen carbonate, nitrate, and hydroxide.

7. The process according to claim 1, wherein the depleted alkali metal catalyst comprises a second metal selected from the group consisting of zirconium, titanium, hafnium, aluminium, boron and magnesium, and mixtures thereof.

8. The process according to claim 1, wherein the polar organic solvent is an alcohol.

9. The process according to claim 1, wherein the solution of the alkali metal salt in the solvent system has a starting pH between 8 and 13.

10. The process according to claim 1, wherein water is present in the solution at up to 40% by weight.

11. The process according to claim 1, wherein the alkali metal salt in solution is <2 wt %.

12. The process according to claim 1, wherein an increase in alkali metal on the catalyst following the process is in the range 0.25 to 2.0 mol %.

13. The process according to claim 1, wherein alkali metal concentration in the solvent system to initially begin impregnation is between $6 \times 10^{-3}$ and 0.6 mol·dm⁻³ alkali metal in the solution.

14. The process according to claim 1, wherein the process is carried out at a temperature of 0-100° C.

15. The process according to claim 1, wherein the process is carried out at a pressure of 1-10 bara.

16. The process according to claim 1, wherein the catalyst is a fixed bed form during contact with the alkali metal solution.

17. The process according to claim 1, wherein flow rates for the alkali metal solution in contact with the catalyst are 0.1 to 10 bed volumes/hr.

18. The process according to claim 1, wherein the catalyst is formed into shaped units having maximum and minimum dimensions in the range 1 to 10 mm.

19. The process according to claim 1, wherein the process is a liquid phase impregnation process.

* * * * *